United States Patent
Studer

(10) Patent No.: US 7,503,248 B2
(45) Date of Patent: Mar. 17, 2009

(54) HOLDING DEVICE HAVING AN OSCILLATORY ULTRAMICROTOME CUTTER

(75) Inventor: Daniel Studer, Dotzigen (CH)

(73) Assignee: Anton Meyer & Co. AG, Nidau (CH)

( * ) Notice: Subject to any disclaimer, the term of this patent is extended or adjusted under 35 U.S.C. 154(b) by 387 days.

(21) Appl. No.: 10/552,620

(22) PCT Filed: Apr. 28, 2004

(86) PCT No.: PCT/CH2004/000256

§ 371 (c)(1),
(2), (4) Date: Oct. 6, 2005

(87) PCT Pub. No.: WO2004/097374

PCT Pub. Date: Nov. 11, 2004

(65) Prior Publication Data

US 2006/0248997 A1    Nov. 9, 2006

(30) Foreign Application Priority Data

May 2, 2003    (CH) ..................... 0771/03

(51) Int. Cl.
*G01N 1/06*    (2006.01)
*B26D 5/00*    (2006.01)

(52) U.S. Cl. .............. 83/703; 83/707; 83/713; 83/915.5

(58) Field of Classification Search ............... 83/915.5, 83/703, 707, 713, 956
See application file for complete search history.

(56) References Cited

U.S. PATENT DOCUMENTS

| | | | |
|---|---|---|---|
| 4,168,577 A | | 9/1979 | Soderkvist et al. |
| 4,377,958 A | * | 3/1983 | Leighton ............... 83/915.5 |
| 4,567,797 A | | 2/1986 | Folk |
| 5,609,083 A | * | 3/1997 | Persson ............... 83/915.5 |
| 2004/0107807 A1 | * | 6/2004 | Studer ............... 83/915.5 |

FOREIGN PATENT DOCUMENTS

| | | |
|---|---|---|
| BE | 440 928 | 4/1941 |
| CH | 690 296 A5 | 7/2000 |
| DE | 3820085 C1 | 7/1989 |
| DE | 19951288 A1 | 5/2001 |
| EP | 0 924 503 A1 | 6/1999 |
| EP | 1 101 577 A1 | 5/2001 |

* cited by examiner

*Primary Examiner*—Stephen Choi
(74) *Attorney, Agent, or Firm*—Rothwell, Figg, Ernst & Manbeck, P.C.

(57) ABSTRACT

A holder provided with an oscillatory movable ultramicrotome cutter which is arranged on a cutter holder and oscillatory movable by means of a piezo-electric element. The cutter is supported by the piezo-electric element. The holder can be easily produced with high dimensional accuracy. It makes it possible to oscillate the cutter blade at a high frequency.

13 Claims, 2 Drawing Sheets

HOLDING DEVICE HAVING AN OSCILLATORY ULTRAMICROTOME CUTTER

CROSS REFERENCE TO RELATED APPLICATIONS

This application is a 35 U.S.C. § 371 National Phase Entry Application from PCT/CH2004/000256, filed Apr. 28, 2004, and designating the U.S.

TECHNICAL FIELD

The invention relates to a holding device having an oscillatory ultramicrotome cutter in accordance with the preamble of patent claim 1.

PRIOR ART

It is proposed in EP-A-0'924'503 to set an ultramicrotome cutter oscillating parallel to its edge, in order to obtain ultrathin sample pieces in a range from 10 to 200 nm and cut in an undistorted fashion. The cutter is fastened on a cutter holder that is connected to a base via a resilient element. Arranged on a second holder likewise connected to the base is a piezoelectric element that exerts a force on the cutter holder in order to set the cutter blade oscillating.

Although good results are obtained in some cases with the aid of ultramicrotome cutters driven in such a way, samples of inadequate cutting quality also keep occurring nevertheless. This is the case, in particular, in cryo-ultramicrotomy, where deep-frozen samples are cut in a temperature range of down to −160° C.

DE-C-38'20'085 discloses an ultramicrotome that has on a base a cutter holder with a cutting edge. The cutter itself is held via bearings, it being possible to move these bearings with the aid of a piezoelectric element.

SUMMARY OF THE INVENTION

It is therefore an object of the invention to improve the holding device for an ultramicrotome cutter of the type mentioned at the beginning.

This object is achieved by a holding device having the features of patent claim 1.

In the holding device according to the invention, the cutter is supported by a piezoelectric element that sets the cutter oscillating. The cutter is preferably otherwise freely suspended. It is therefore supported exclusively by the piezoelectric element.

As a result, the piezoelectric element need move only a relatively slight mass. It is therefore possible to achieve relatively high frequencies, and the movement can be executed in a more targeted fashion. Drifting can be reduced to a minimum.

Ultrathin sections or sample pieces can be obtained. The sections obtained are regular, and the sample piece cut is not compressed but maintains it original shape. The holding device according to the invention is suitable, even though not exclusively, for use in cryo-ultramicrotomy.

A further advantage is that the holding device according to the invention has a very simple design. It can therefore be produced with the highest accuracy and yet in a relatively cost-effective fashion.

It is preferred to make use of so-called shear piezoelectric crystals or piezoelectric ceramics that expand or contract in a direction perpendicular to the applied voltage, that is to say execute a shearing movement. An oscillating movement parallel to the cutter edge can be achieved in a simple way by means of these piezoelectric elements.

Further advantageous embodiments are laid down in the dependent patent claims.

BRIEF DESCRIPTION OF THE DRAWINGS

The subject matter of the invention is explained below with the aid of preferred exemplary embodiments that are illustrated in the attached drawings, in which:

FIG. 1b shows a partial section through the holding device in accordance with FIG. 1a;

FIG. 2b shows an exploded view of FIG. 2a;

WAYS OF IMPLEMENTING THE INVENTION

Figure 1A:
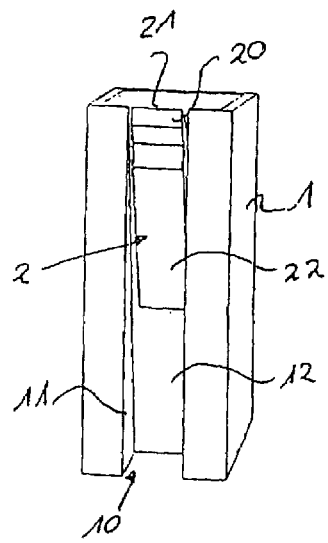
FIG. 1a shows a perspective view of a holding device according to the invention from the front, in a first embodiment.
Figure 1B:
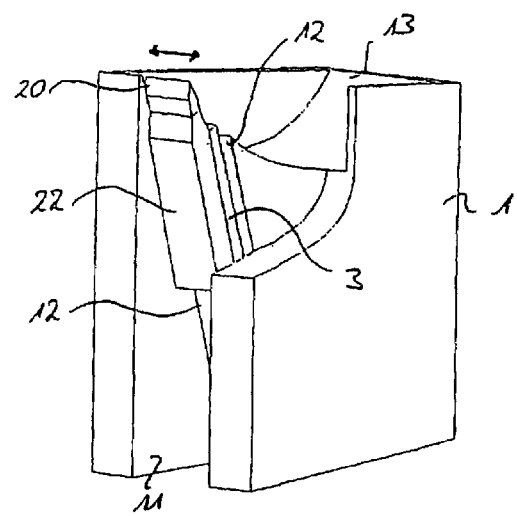

FIGS. 1a and 1b show a holding device according to the present invention in accordance with a first preferred embodiment. The holding device has a cutter holder 1, a cutter 2 and a first piezoelectric element 3.

The cutter holder 1 is preferably produced from a metal or from a plastic and preferably has a cuboidal basic shape. It has on one end face a groove 10 that is bounded by side walls 11 and a groove base 12. The side walls 11 preferably run parallel to one another, and preferably form an at least approximately right angle with the groove base 12. The groove base 12 is designed as an oblique surface, i.e. it runs inclined to the side walls 11. The cutter holder 1 can have a depression 13 behind the groove 10 at one end of the groove base 12. If the cutter is used in classical ultramicrotomy, this depression 13 serves for holding water. Cut sample pieces float on this water. The depression is superfluous if the cutter is used in cryo-ultramicrotomy. The cut sample pieces slide in this case on the cutter surface, from which they are lifted off.

The piezoelectric element 3 is fastened on the groove base 12. It is preferably bonded fast thereon. Suitable for this purpose are all known adhesives that promote a sufficiently strong connection. Particularly in the case of low temperature applications, the adhesive must be resistant even for high temperature differences, which can certainly amount to up to 180° C., specifically from −160° C. up to room temperature.

The piezoelectric element 3 is preferably designed as a flat cuboid with plane-parallel first and second supporting surfaces 30, 31. It is bonded to the cutter holder 1 with the first supporting surface 30, while the cutter 2 is bonded on the second supporting surface 31 and is thereby supported by the piezoelectric element 3 and is otherwise freely suspended. Other types of fastening can be used on both sides. The piezoelectric element 3 is a shear piezoelectric element here. Given an applied electric field, it therefore executes a shear movement perpendicular to the field lines. The shear piezoelectric element can be of single-layer or multilayer type. Metal layers at which contact wires are fitted are pre-deposited on both lateral surfaces, which here form the supporting surfaces 30, 31.

In the cutter holder 1, movement of the piezoelectric element is at least approximately, preferably precisely, parallel to the groove base 12. For this purpose, the groove 12 has a width that is greater than the width of the piezoelectric element 3 and than the width of a blade holder 22, described below, of the cutter 2. Typical oscillation frequencies lie between 30 kHz and 200 kHz. High frequencies have the advantage that the drift is relatively low, and that the quality of the cut sample pieces, that is to say the cuts, is high.

The cutter 2 has a preferably cuboidal blade holder 22, and a blade 20 arranged thereon and with a cutting edge 21. The cutting edge 21 runs at least approximately parallel to the second bearing surface 31 of the piezoelectric element 3, thus also to the groove base 12. If an AC voltage is applied to the piezoelectric element 3, the cutter oscillates in a fashion at least approximately parallel, preferably precisely parallel, to the direction in which its cutting edge 21 extends. This is illustrated by an arrow in the figure.

The blade holder 22 and the blade 20 can be of unipartite design (made in one piece). However, it is also possible for them to be of multipartite design so that the blade 20 can be exchanged per se. If they are of unipartite design, the entire holding device is preferably exchanged. At least the blade 20 preferably consists of diamond.

Figure 2A:
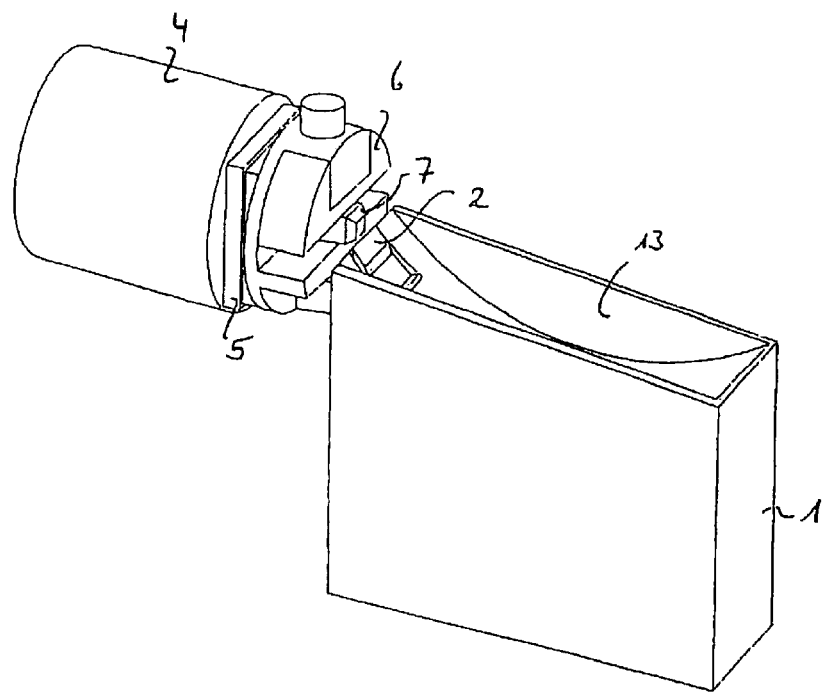
FIG. 2a shows a perspective view of the holding device in accordance with FIG. 1a and of a sample holding device.
Figure 2B:
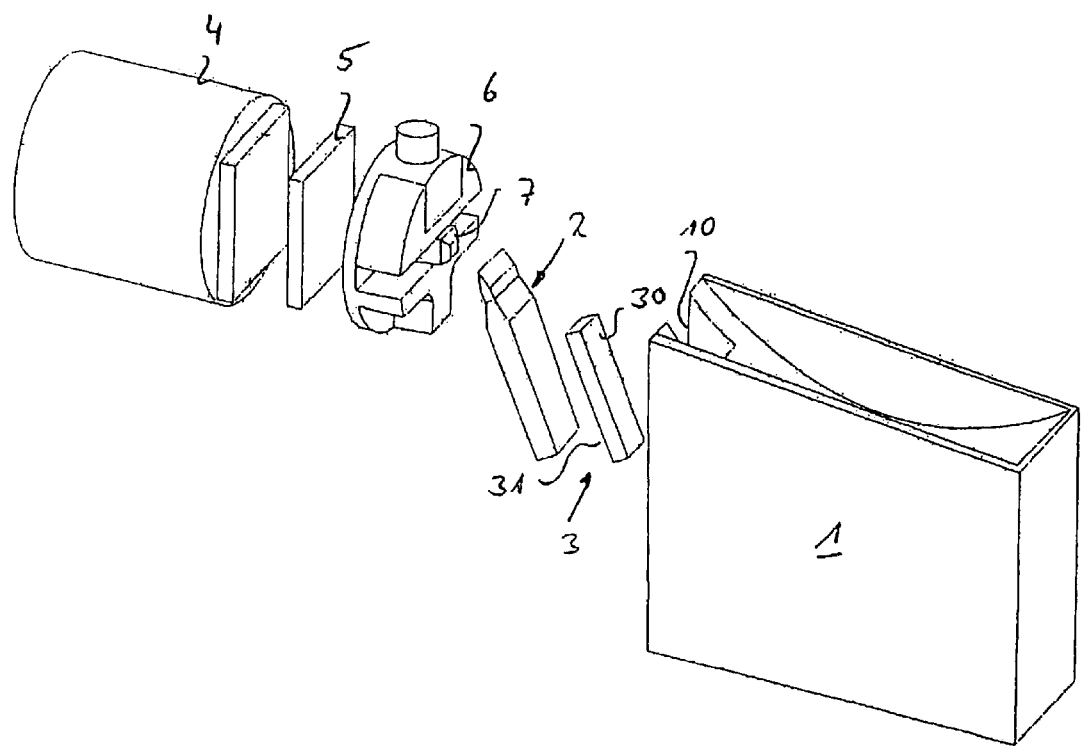

The holding device is illustrated in FIGS. 2a and 2b in a fashion operationally connected to a sample 7 to be cut. The sample 7 can be any desired material for which the aim is to cut off an ultrathin slice for the purpose of analysis under a suitable microscope. As mentioned at the beginning, it is possible to achieve at least cut thicknesses of between 10 to 100 nm, the quality of the ultrathin cuts being improved with the aid of the holding device according to the invention. The sample is usually a tissue or some other organic material. However, it is also possible for inorganic materials to be cut in this way.

The sample 7 is held in a sample holder 6 that is fastened on a sample holder block 4. The sample holder block 4 and the cutter holder 1 can, but need not, be arranged on the same base (not illustrated here) of the ultramicrotome. In one variant of the method, during cutting the sample 7 remains at rest and only the cutter oscillates. In another variant, the sample 7 also oscillates. It is possible for this purpose to arrange between the sample holder 6 and sample holder block 4 a second piezoelectric element 5, preferably also a shear piezoelectric element. Consequently, the sample 7 can likewise move in a simple way in a direction at least approximately parallel to the edge 21. The sample 7 then preferably moves in the opposite direction to the cutter 2. It is also possible to set the sample 7 oscillating with a time offset in the same direction or the opposite one such that the sample 7 moves at the reversal point of the cutter 2, and the cutter 2 moves at the reversal point of the sample 7.

Figure 3:
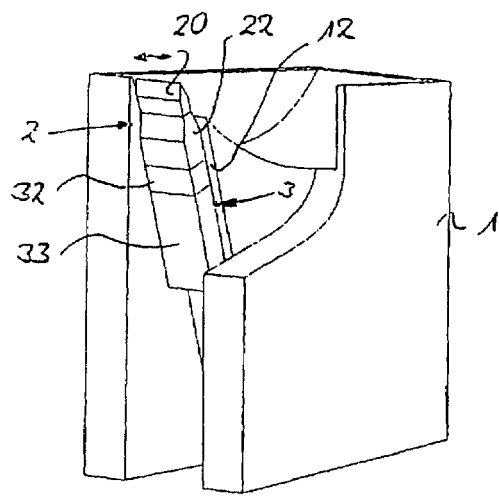
FIG. 3 shows a partial section through a holding device according to the invention, in accordance with a second embodiment.

A second preferred exemplary embodiment of the holding device according to the invention is illustrated in FIG. 3. This holding device differs from the first exemplary embodiment in that the piezoelectric element 3 is now no longer arranged in the shape of a flat cuboid between the groove base 12 and cutter 2. Rather, the piezoelectric element 3 is now arranged at an end of the blade holder 22 that is on its opposite end viewed from the blade 20. This embodiment has the advantage that the cutter 2 can itself be of very short design such that the mass to be moved is minimized. Since the cutter can be fastened in advance on the piezoelectric element, and it is only at the end that the unit formed by the cutter and piezoelectric element need be fastened on the cutter holder, the production is additionally facilitated and the measuring accuracy is increased. Also quality assurance is improved, since the cutter/piezoelectric element unit can be tested by itself before installation in the cutter holder 1.

In an embodiment not illustrated here, the piezoelectric crystal or piezoelectric ceramic is bonded directly to the groove base 12. However, the piezoelectric element 3 preferably has not only a piezoelectric crystal or a piezoelectric ceramic 32 but also a piezo holder 33, as illustrated here. This piezo holder 33 is of cuboidal design and is bonded with a preferably wide supporting surface to the groove base 12. This has the advantage that it is possible to use a relatively small piezoelectric crystal or a small piezoelectric ceramic 32 but that a sufficiently large area serves nevertheless as a bonding area. The cutter 2 oscillates freely with reference to the groove base 12. The groove base 12 can therefore have a corresponding step (not illustrated here).

In the examples described above, the cutter holder 1 has the groove 10. This groove 10 has the advantage that it serves as a guide aid when fastening the piezoelectric element and the cutter. However, the groove 10 is not mandatory. The cutter holder 1 can also basically have another shape. All that is essential is that the piezoelectric element needs to move only the cutter and no further elements, or as few further elements as possible.

Figure 4:
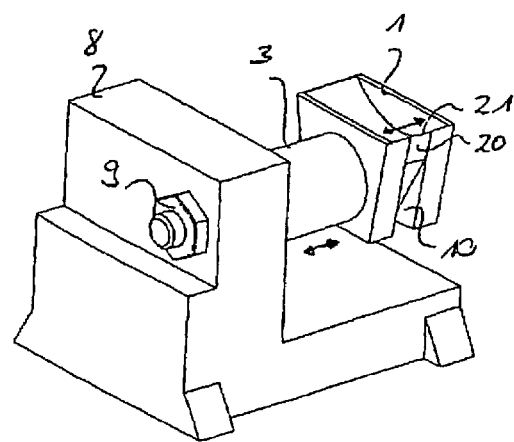
FIG. 4 shows a perspective view of a holding device according to the invention, in accordance with a third embodiment.

A third embodiment is illustrated in FIG. 4. Here, the holding device according to the invention has a cutter holder block 8 on which the piezoelectric element 3 is fastened. It may in turn be bonded, but here it is screwed. The cutter holder 1 with the cutter 2 fastened, in particular bonded, therein in a fixed position is arranged freely suspended on the piezoelectric element 3. By applying an AC voltage to the piezoelectric element 3, it is possible, in turn, to set the cutter blade 20 oscillating parallel to its longitudinal direction, as illustrated by an arrow. In this embodiment, it is also possible to use as the piezoelectric element a crystal or a ceramic that expands in a direction parallel to the applied electric field. It is preferred to use a multilayer element. It is an advantageous feature of the embodiment illustrated that the cutter holder forms a screw head, the associated screw body penetrating the piezoelectric element and being held on the opposite side by a lock nut 9 braced against the cutter holder block 8. This arrangement has the advantage that the required pressure build-up in the piezoelectric element is achieved, and the cutter can be held, with one and the same element.

The holding device according to the invention can be produced simply and with high dimensional accuracy. It also permits the cutter edge to oscillate at a high frequency.

LIST OF REFERENCE NUMERALS

1 Cutter holder
10 Groove
11 Side walls
12 Groove base
13 Depression
2 Cutter
20 Blade
21 Cutting edge
22 Blade holder
3 First piezoelectric element
30 First supporting surface
31 Second supporting surface
32 Piezoelectric crystal
33 Piezoelectric holder
4 Sample holder block
5 Second piezoelectric element
6 Sample holder
7 Sample 8 Cutter holder block
9 Lock nut

The invention claimed is:

1. A holding device for an ultramicrotome, the device comprising:
   a cutter having a cutting edge,
   a stationary cutter holder, and
   a piezoelectric element, the piezoelectric element having a first supporting surface and a second supporting surface, the first supporting surface being fastened on the cutter holder and the cutter being fastened on the second supporting surface, the piezoelectric element being adapted to oscillate said cutter relative to said cutter holder,
   wherein the cutter is supported on the cutter holder exclusively by the piezoelectric element and is otherwise freely suspended on said cutter holder.

2. The holding device as claimed in claim 1, wherein the cutter is made in one piece.

3. The holding device as claimed in claim 2, wherein the cutter consists of diamond.

4. The holding device as claimed in claim 1, wherein the piezoelectric element is adapted to oscillate the cutter along a direction that is substantially parallel to the cutting edge.

5. The holding device as claimed in claim 4, characterized in that the piezoelectric element (3) has a piezoelectric crystal or a piezoelectric ceramic (32) that is operable in a shear mode.

6. The holding device as claimed in claim 1, wherein the second supporting surface is parallel to the first supporting surface, and wherein the cutting edge extends along a direction that is substantially parallel to the first and second supporting surfaces.

7. The holding device as claimed in claim 1, wherein the cutter holder has a groove having two side walls and a groove base, the groove base forming an oblique surface, the piezoelectric element being fastened to said surface.

8. The holding device as claimed in claim 7, the cutter being made in one piece and having a predetermined width, and the groove having a width that is greater than the width of the cutter.

9. The holding device as claimed in claim 7, the cutter comprising a blade holder and a blade, the blade being mounted on said blade holder, the blade holder having a predetermined width, and the groove having a width that is greater than the width of said blade holder.

10. The holding device as claimed in claim 1, characterized in that the piezoelectric element (3) has a piezoelectric crystal or a piezoelectric ceramic (32) and a piezo holder (33), in that the cutter (2) is fastened on the piezoelectric crystal or on the piezoelectric ceramic (32), and in that the piezo holder (33) is arranged on the cutter holder (1).

11. The holding device as claimed in claim 1, the cutter comprising a blade holder and a blade, the blade defining said cutting edge, and the blade being mounted on said blade holder.

12. The holding device as claimed in claim 11, wherein the blade is removable from said blade holder.

13. An ultramicrotome comprising
   a holding device as claimed in claim 1,
   a sample holder block,
   an oscillatory sample holder for holding a sample to be cut by means of the cutter and
   a second piezoelectric element, the sample holder being fastened to said sample holder block and being supported on said sample holder block exclusively by said second piezoelectric element, being otherwise freely suspended,
   the second piezoelectric element being operable in a shear mode.

* * * * *